(12) United States Patent
Foad et al.

(10) Patent No.: US 7,977,199 B2
(45) Date of Patent: *Jul. 12, 2011

(54) METHOD FOR MEASURING DOPANT CONCENTRATION DURING PLASMA ION IMPLANTATION

(75) Inventors: Majeed A. Foad, Sunnyvale, CA (US); Shijian Li, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/777,085

(22) Filed: May 10, 2010

(65) Prior Publication Data

US 2010/0216258 A1    Aug. 26, 2010

Related U.S. Application Data

(63) Continuation of application No. 12/049,047, filed on Mar. 14, 2008, now Pat. No. 7,713,757.

(51) Int. Cl.
*H01L 21/00* (2006.01)
(52) U.S. Cl. ...... 438/306; 438/7; 438/547; 257/E21.528
(58) Field of Classification Search .............. 438/7, 306, 438/547, 798; 257/E21.528
See application file for complete search history.

(56) References Cited

U.S. PATENT DOCUMENTS

| | | | |
|---|---|---|---|
| 4,962,461 A | 10/1990 | Meyer et al. | |
| 5,423,945 A | 6/1995 | Marks et al. | |
| 5,665,640 A | 9/1997 | Foster et al. | |
| 6,101,971 A | 8/2000 | Denholm et al. | |
| 6,174,450 B1 | 1/2001 | Patrick et al. | |
| 6,286,362 B1 | 9/2001 | Coffman et al. | |
| 6,313,002 B1 | 11/2001 | Fukuda | |
| 6,323,951 B1 | 11/2001 | Borden et al. | |
| 6,350,697 B1 | 2/2002 | Richardson et al. | |
| 6,395,150 B1 | 5/2002 | Van Cleemput et al. | |
| 6,413,321 B1 | 7/2002 | Kim et al. | |

(Continued)

FOREIGN PATENT DOCUMENTS

EP    0942453    9/1999

(Continued)

OTHER PUBLICATIONS

PCT International Search Report and Written Opinion dated Mar. 5, 2010 for International Application No. PCT/US2009/034995.

(Continued)

*Primary Examiner* — Fernando L Toledo
(74) *Attorney, Agent, or Firm* — Patterson & Sheridan, L.L.P.

(57) ABSTRACT

Embodiments of the invention generally provide methods for end point detection at predetermined dopant concentrations during plasma doping processes. In one embodiment, a method includes positioning a substrate within a process chamber, generating a plasma above the substrate and transmitting a light generated by the plasma through the substrate, wherein the light enters the topside and exits the backside of the substrate, and receiving the light by a sensor positioned below the substrate. The method further provides generating a signal proportional to the light received by the sensor, implanting the substrate with a dopant during a doping process, generating multiple light signals proportional to a decreasing amount of the light received by the sensor during the doping process, generating an end point signal proportional to the light received by the sensor once the substrate has a final dopant concentration, and ceasing the doping process.

20 Claims, 10 Drawing Sheets

U.S. PATENT DOCUMENTS

| | | |
|---|---|---|
| 6,461,972 B1 | 10/2002 | Kabansky |
| 6,531,681 B1 | 3/2003 | Markle et al. |
| 6,559,026 B1 | 5/2003 | Rossman et al. |
| 6,579,805 B1 | 6/2003 | Bar-Gadda |
| 6,617,794 B2 | 9/2003 | Barnes et al. |
| 6,627,463 B1 | 9/2003 | Sarfaty |
| 6,649,075 B1 | 11/2003 | Buie et al. |
| 6,747,245 B2 | 6/2004 | Talwar et al. |
| 6,800,559 B2 | 10/2004 | Bar-Gadda |
| 6,870,170 B1 | 3/2005 | Farley et al. |
| 6,965,116 B1 | 11/2005 | Wagner et al. |
| 7,037,813 B2 | 5/2006 | Collins et al. |
| 7,078,711 B2 | 7/2006 | Borden |
| 7,137,354 B2 | 11/2006 | Collins et al. |
| 7,173,757 B2 | 2/2007 | Kim et al. |
| 7,303,982 B2 | 12/2007 | Collins et al. |
| 7,713,757 B2 * | 5/2010 | Foad et al. ............ 438/7 |
| 2003/0013260 A1 | 1/2003 | Gossmann et al. |
| 2003/0013314 A1 | 1/2003 | Ying et al. |
| 2003/0085205 A1 | 5/2003 | Lai et al. |
| 2003/0153101 A1 | 8/2003 | Takase et al. |
| 2004/0084427 A1 | 5/2004 | Talwar et al. |
| 2005/0051271 A1 | 3/2005 | Collins et al. |
| 2005/0140976 A1 | 6/2005 | Hovinen et al. |
| 2005/0230047 A1 | 10/2005 | Collins et al. |
| 2006/0081558 A1 | 4/2006 | Collins et al. |
| 2006/0088655 A1 | 4/2006 | Collins et al. |
| 2006/0102607 A1 | 5/2006 | Adams et al. |
| 2007/0224840 A1 | 9/2007 | Renau et al. |
| 2008/0026133 A1 | 1/2008 | Fang et al. |
| 2008/0075834 A1 | 3/2008 | Ramaswamy et al. |
| 2008/0188013 A1 | 8/2008 | Cho et al. |
| 2009/0233384 A1 | 9/2009 | Foad et al. |

FOREIGN PATENT DOCUMENTS

| | | |
|---|---|---|
| EP | 1158071 | 11/2001 |
| JP | 0704555 | 1/1995 |
| JP | 2000150908 | 5/2000 |

OTHER PUBLICATIONS

Sobolewski "Measuring the Ion Current in High-Density Plasmas Using Radio-Frequency Current and Voltage Measurements." Journal of Applied Physics, vol. 90, No. 6, Sep. 15, 2001, pp. 2660-2671.

* cited by examiner

METHOD FOR MEASURING DOPANT CONCENTRATION DURING PLASMA ION IMPLANTATION

CROSS-REFERENCE TO RELATED APPLICATION

This application is a continuation of U.S. Ser. No. 12/049,047, filed Mar. 14, 2008, and issued as U.S. Pat. No. 7,713,757, which is incorporated herein by reference in its entirety.

BACKGROUND OF THE INVENTION

1. Field of the Invention

Embodiments of the invention generally relate to methods for processing a substrate, and more particularly, to methods for measuring a dopant concentration of a substrate during a doping process.

2. Description of the Related Art

It is important to control ion dosage during plasma processes, such as plasma-enhanced chemical vapor deposition (PE-CVD) process, high density plasma chemical vapor deposition (HDP-CVD) process, plasma immersion ion implantation process (P3I), and plasma etch process. Ion implantation processes in integrated circuit fabrication particularly require instrumentation and control to achieve a desired ion dose on a semiconductor substrate.

The dose in ion implantation generally refers to the total number of ions per unit area passing through a surface plane of the substrate being processing. The implanted ions distribute themselves throughout the volume of the substrate. The principal variation in implanted ion density (number of ions per unit volume) occurs along the direction of the ion flux, usually the perpendicular (vertical) direction relative to the substrate surface. The distribution of ion density (ions per unit volume) along the vertical direction is referred to as the ion implantation depth profile. Instrumentation and control systems for regulating ion implant dose (ions per unit area) are sometimes referred to as dosimetry.

Ion implantation may be performed in ion beam implant apparatus and in plasma immersion ion implantation apparatus. Ion beam implant apparatus, which generate a narrow ion beam that must be raster-scanned over the surface of the substrate, typically implant only a single atomic species at one time. The ion current in such an apparatus is precisely measured and integrated over time to compute the actual dose. Because the entire ion beam impacts the substrate and because the atomic species in the beam is known, the ion implant dose can be accurately determined. This is critical in an ion beam implant apparatus, because it employs a DC ion source, which is subject to significant drift in its output current, and the various grids and electrodes employed in the beam implant machine drift as well (due to the susceptibility of a DC source to accumulation of deposited material on component surfaces). Accordingly, precise dosimetry is essential in an ion beam implant apparatus. The precisely monitored ion beam current is integrated over time to compute an instantaneous current implant dose, and the process is halted as soon as the dose reaches a predetermined target value.

In contrast, plasma immersion ion implantation reactors present a difficult problem in dosimetry. Typically, the atomic weight of the ions incident on the substrate cannot be precisely determined because such a reactor employs a precursor gas containing the desired ion implantation species as well as other species. For example, plasma immersion ion implantation of boron usually employs a multi-element compound, such as the precursor diborane, so that both boron and hydrogen ions may be incident on the substrate. As a result, determining the boron dose from a measured current is difficult. Another difficulty in implementing dosimetry in a plasma immersion ion implantation reactor is that the plasma ions impact the entire substrate continuously, so that it is difficult to effect a direct measurement above the substrate of the total ion current to the substrate. Instead, the dose must be indirectly inferred from measurements taken over a very small area. This is particularly true of reactors employing RF (radio frequency) plasma source power or RF plasma bias power.

Therefore, there is a need for a method for determining an end point at a predetermined dopant concentration during a plasma doping process.

SUMMARY OF THE INVENTION

Embodiments of the invention generally provide methods and apparatuses for end point detection at predetermined dopant concentrations during plasma doping processes. In one embodiment, a method for detecting a doping concentration on a substrate surface during a plasma doping process is provided which includes positioning a substrate within a process chamber, wherein the substrate has a topside and a backside and is at a temperature of less than about 250° C., generating a plasma above the substrate within the process chamber, transmitting a light generated by the plasma through the substrate, wherein the light enters the topside and exits the backside of the substrate, and receiving the light by a sensor positioned below the substrate. The method further provides generating a signal proportional to the light received by the sensor, implanting the substrate with a dopant during a doping process, generating multiple light signals proportional to a decreasing amount of the light received by the sensor during the doping process, generating an end point signal proportional to the light received by the sensor once the substrate has a final concentration of the dopant, and ceasing the dopant implantation of the substrate.

In some embodiments, the method may include generating multiple signals proportional to an increasing dopant concentration. The light generated by the plasma may contain infrared light, visible light, ultraviolet light, or combinations thereof. In one example, the light contains infrared light. Usually, the temperature of the substrate during the plasma doping process may be within a range from about 0° C. to about 90° C., preferably, about 25° C. to about 45° C., during the doping process.

In some embodiments, the dopant may be boron, phosphorous, arsenic, antimony, nitrogen, oxygen, hydrogen, carbon, germanium, or combinations thereof. The final concentration of the dopant may be within a range from about $1 \times 10^{14}$ cm$^{-2}$ to about $1 \times 10^{18}$ cm$^{-2}$, preferably, from about $5 \times 10^{15}$ cm$^{-2}$ to about $1 \times 10^{17}$ cm$^{-2}$. In one example, the dopant is boron and the doping process includes exposing the substrate to a boron precursor, such as trifluoroborane, diborane, plasmas thereof, derivatives thereof, or combinations thereof. In another example, the dopant is phosphorous and the doping process includes exposing the substrate to a phosphorous precursor, such as trifluorophosphine, phosphine, plasmas thereof, derivatives thereof, or combinations thereof. In another example, the dopant is arsenic and the doping process includes exposing the substrate to an arsenic precursor, such as arsine, plasmas thereof, or derivatives thereof.

In another embodiment, a method for detecting a doping concentration on a substrate surface during a plasma doping process is provided which includes positioning a substrate within a process chamber, wherein the substrate has a topside and a backside and is at a temperature of less than about 250° C., generating a plasma above the substrate within the process chamber, transmitting a light through the substrate, wherein the light enters the backside and exits the topside of the substrate and the light is generated by a light source positioned below the substrate, and receiving the light by a sensor positioned above the substrate. The method further provides generating a signal proportional to the light received by the sensor, implanting the substrate with a dopant during a doping process, generating multiple light signals proportional to a decreasing amount of the light received by the sensor during the doping process, generating an end point signal proportional to the light received by the sensor once the substrate has a final concentration of the dopant, and ceasing the dopant implantation of the substrate.

Embodiments provide that the light source may be a laser, such as an infrared laser. The light may contain infrared light, visible light, ultraviolet light, or combinations thereof. In one example, the sensor may be disposed on or coupled to a showerhead assembly (e.g., gas distribution assembly) within the process chamber. The light source may be coupled to, within, or disposed on a substrate support assembly. The substrate support assembly may have an electrostatic chuck.

In a specific example, the sensor is disposed on or in a showerhead assembly and the light source is positioned to direct the light substantially towards the sensor. The light source may be an optical cable coupled to a remote light source, such as a laser source which emits a laser beam. In some embodiments, the magnitude of the plasma light signal may be subtracted from the magnitude of the light signal during a calibration step.

In another embodiment, a method for detecting a doping concentration on a substrate surface during a plasma doping process is provided which includes positioning a substrate within a process chamber, wherein the substrate has a topside and a backside and is at a temperature of less than about 250° C., generating a plasma above the substrate within the process chamber, and transmitting a light through the substrate. The method further provides receiving the light by a sensor, generating an initial signal proportional to the light received by the sensor, implanting the substrate with a dopant during a dopant process, modulating the light received by the sensor proportional to an increasing dopant concentration, generating an end point signal proportional to the light received by the sensor once the substrate has a final concentration of the dopant, and ceasing the dopant implantation of the substrate.

In one example, the light is generated by the plasma, the light received by the sensor is decreasing proportional to the increasing dopant concentration, and the sensor is positioned below the substrate. In another example, the light is generated by a light source (e.g., laser source) positioned below the substrate, the light received by the sensor is decreasing proportional to the increasing dopant concentration, and the sensor is positioned below the substrate. In another example, the light is generated by a light source positioned above the substrate, the light received by the sensor is increasing proportional to the increasing dopant concentration, and the sensor is positioned above the substrate.

In another embodiment, a method for detecting a doping concentration on a substrate surface during a plasma doping process is provided which includes positioning a substrate within a process chamber, wherein the substrate has a topside and a backside and is at a temperature of less than about 250° C., generating a plasma above the substrate within the process chamber, generating a light by a light source positioned above the substrate, transmitting the light from the light source to the topside of the substrate, and reflecting the light from the topside towards a sensor positioned above the substrate. The method further provides generating a signal proportional to the light received by the sensor, implanting the substrate with a dopant during a doping process, generating multiple light signals proportional to an increasing amount of the light received by the sensor during the doping process, generating an end point signal proportional to the light received by the sensor once the substrate has a final concentration of the dopant, and ceasing the dopant implantation of the substrate.

Embodiments provide that the light may be shined towards the topside of the substrate at an angle within a range from about 45° to about 90° relative to a plane expanding across the topside of the substrate. Preferably, the angle may be within a range from about 75° to about 90°, and more preferably, substantially about 90°. In one example, the light source may be coupled to or within the showerhead assembly, the sensor may be disposed on or coupled to the showerhead assembly, and the light source may be positioned to reflect the light off the substrate and towards the sensor.

In another embodiment, a method for detecting a doping concentration on a substrate surface during a plasma doping process is provided which includes positioning a substrate within a process chamber, wherein the substrate has a topside and a backside and is at a temperature of less than about 250° C., generating a plasma above the substrate within the process chamber, reflecting a light from the topside of the substrate, and receiving the light by a sensor. The method further provides generating an initial signal proportional to the light received by the sensor, implanting the substrate with a dopant during a dopant process, increasing the light received by the sensor proportional to an increasing dopant concentration, generating an end point signal proportional to the light received by the sensor once the substrate has a final concentration of the dopant, and ceasing the dopant implantation of the substrate.

BRIEF DESCRIPTION OF THE DRAWINGS

So that the manner in which the above recited features of the invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the invention provide methods and apparatuses for measuring a doping concentration in a plasma ion implantation system using an optical sensor. An end point of the plasma ion implantation can be thereby controlled in an effective manner.

Figure 1:
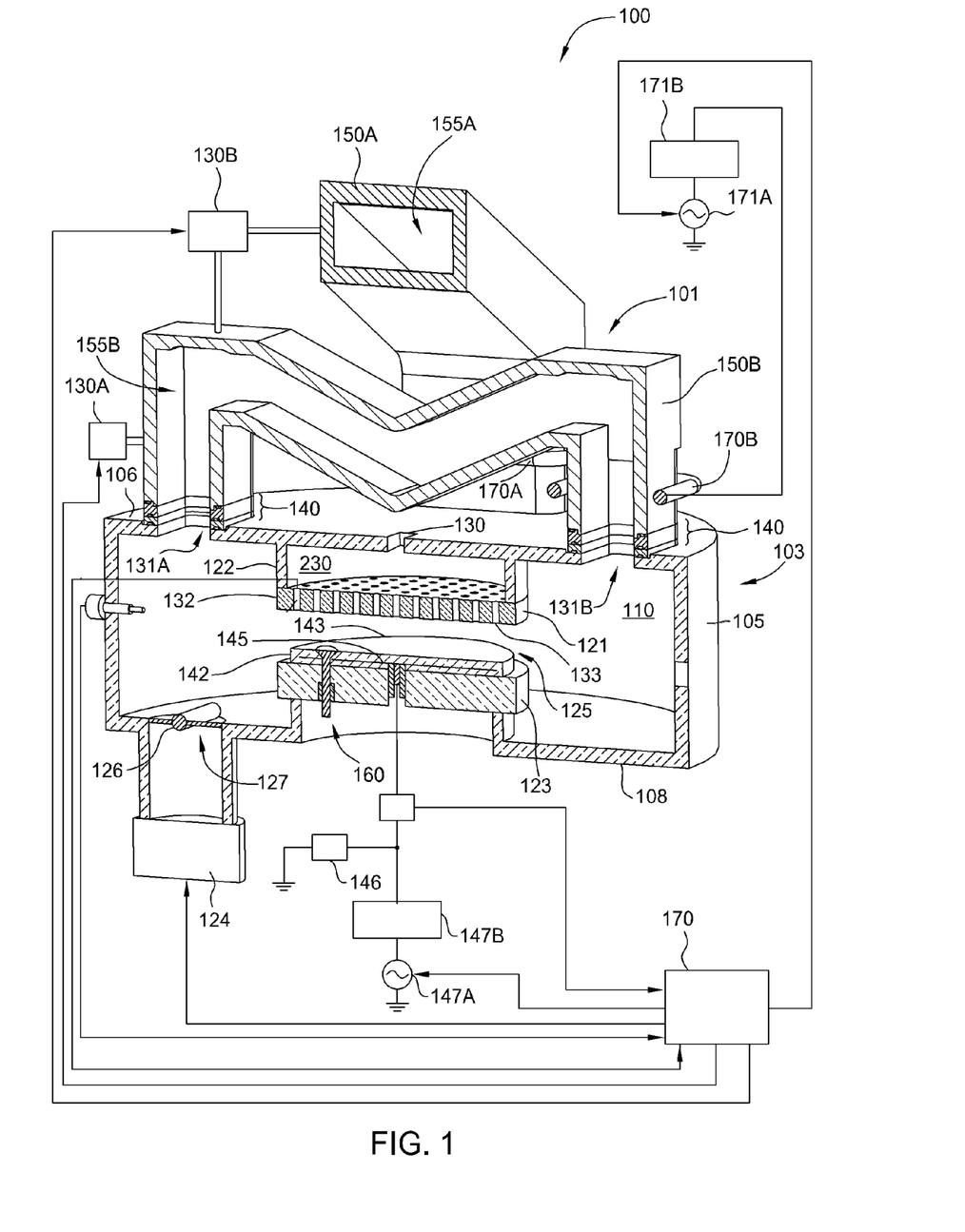
FIG. 1 schematically illustrates an isometric cross-sectional view of a plasma chamber in accordance with one embodiment of the invention.

FIG. 1 schematically illustrates an isometric cross-sectional view of a plasma chamber 100 in accordance with one embodiment of the invention. Plasma chamber 100 may be configured for a plasma-enhanced chemical vapor deposition (PE-CVD) process, a high density plasma chemical vapor deposition (HDP-CVD) process, a plasma-enhanced atomic layer deposition (PE-ALD) process, an ion implantation process, an etch process, and other plasma processes.

Plasma chamber 100 contains a toroidal plasma source 100 coupled to body 102 of plasma chamber 100. Body 102 contains sidewalls 104 coupled to lid 106 and bottom 108, which bounds interior volume 110. Other examples of plasma chamber 100 may be found in U.S. Pat. Nos. 6,939,434, and 6,893,907, which are incorporated by reference herein in their entireties.

Interior volume 120 includes processing region 125 formed between gas distribution assembly 121 (e.g., showerhead assembly) and substrate support assembly 123. Pumping region 122 surrounds a portion of substrate support assembly 123. Pumping region 122 is in selective communication with vacuum pump 124 through valve 126 disposed in port 127 formed in bottom 128. In one embodiment, valve 126 is a throttle valve adapted to control the flow of gas or vapor from interior volume 120 and through port 127 to vacuum pump 124. In one embodiment, valve 126 operates without the use of o-rings, and is further described in U.S. Ser. No. 11/115,956, filed Apr. 26, 2005, and published as U.S. Pub. No. 2006-0237136, which is incorporated by reference in its entirety.

Figure 2:
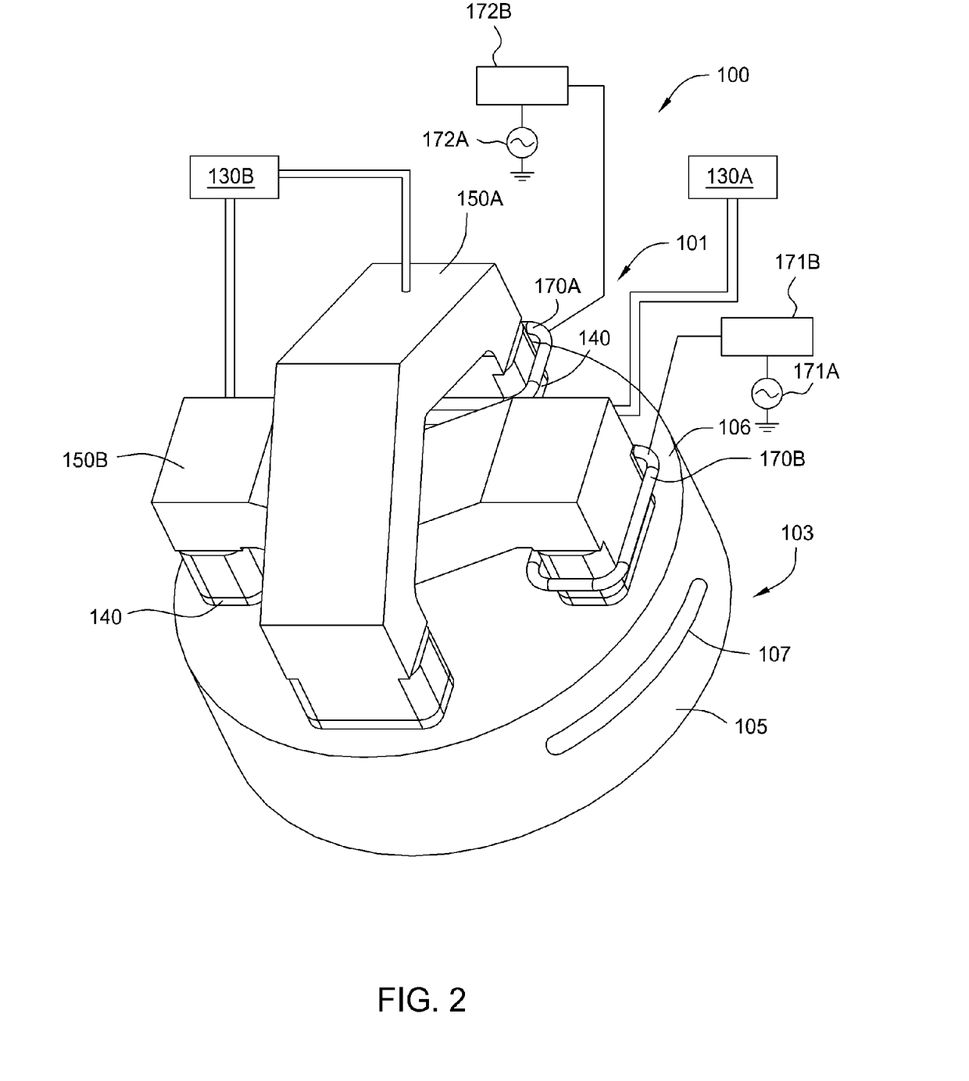
FIG. 2 schematically illustrates an isometric top view of the plasma chamber of FIG. 1.

Toroidal plasma source 101 is disposed on lid 106 of body 110. In one embodiment, toroidal plasma source 101 has first conduit 150A having a general "U" shape, and second conduit 150B having a general "M" shape. First conduit 150A and second conduit 150B each include at least one antenna 170A and 170B, respectively. Antennas 170A and 170B are configured to form an inductively coupled plasma within interior region 155A/155B of each of conduits 150A/150B, respectively. As shown in FIG. 2, each antenna 170A/170B may be a winding or a coil coupled to a power source, such as RF plasma power source 171A/172A. An RF impedance matching systems 171B/172B may also be coupled to each antenna 170A/170B. Process gases, such as helium, argon, and other gases, may be provided to interior region 155A, 155B of each of the conduits 150A, 150B, respectively. In one embodiment, the process gases may contain a dopant precursor gases that is supplied to interior regions 155A/155B of each conduit 150A/150B. In one embodiment, the process gases may be delivered to toroidal plasma source 101 from gas panel 136. In another embodiment, the process gases may be delivered through gas distribution assembly 121 from gas panel 135 connected to port 130 formed in body 110 of plasma chamber 100.

In one embodiment, each opposing end of the conduits 150A/150B are coupled to respective ports 131A-131D (only 131A and 131B are shown in this view) formed in lid 106 of plasma chamber 100. During processing, a process gas is supplied to the interior region 155A/155B of each of conduits 150A/150B, and RF power is applied to each antenna 170A/170B, to generate a circulating plasma path that travels through ports 131A-131D and processing region 125. Specifically, in FIG. 1, the circulating plasma path travels through port 131A to port 131B, or vise versa, through processing region 125 between gas distribution assembly 121 and substrate support assembly 123. Each conduit 150A/150B has a plasma channeling means 140 coupled between respective ends of conduit 150A/150B and ports 131A-131D. In one embodiment, plasma channel 140 is configured to split and widen the plasma path formed within each of the conduits 150A/150B.

Gas distribution assembly 121 has annular wall 122 and perforated plate 132. Annular wall 122, perforated plate 132 and lid 106 define plenum 134. Perforated plate 132 includes a plurality of openings 133 formed therethrough in a symmetrical or non-symmetrical pattern or patterns. In one embodiment, the dopant precursor gases may be delivered to processing region 125 from gas distribution assembly 121 connected to gas panel 130A. The process gases, such as the dopant precursor gases, may be provided to plenum 134 from port 130. Generally, the dopant precursor gas contains a dopant precursor of the desired dopant element, such as boron (a p-type conductivity impurity in silicon) or phosphorus (an n-type conductivity impurity in silicon). Fluorides and/or hydrides of boron, phosphorous or other dopant elements, such as arsenic, antimony, may be used as a dopant precursor gas. For example, the dopant precursor gas may contain boron trifluoride ($BF_3$) or diborane ($B_2H_6$) while implanting a boron dopant. The gases may flow through openings 133 and into processing region 125 below perforated plate 132. In one embodiment, perforated plate 132 is RF biased to help generate and/or maintain a plasma in processing region 125.

Substrate support assembly 123 has upper plate 142 and cathode assembly 144. Upper plate 142 has a smooth substrate supporting surface 143 configured to support a substrate thereon. Upper plate 142 has an embedded electrode 145 which is connected to a DC power source 146 to facilitate electrostatic attraction between a substrate and substrate supporting surface 143 of upper plate 142 during process. In one embodiment, embedded electrode 145 may also be used as an electrode for providing capacitive RF energy to processing region 125. Embedded electrode 145 may be coupled to a RF plasma bias power 147A via an RF impedance matching circuit 147B.

Substrate support assembly 123 may also include lift pin assembly 160 that contains a plurality of lift pins 162 configured to transfer one or more substrates by selectively lifting and supporting a substrate above upper plate 142 and are spaced to allow a robot blade to position therebetween.

FIG. 2 schematically illustrates an isometric top view of plasma chamber 100 shown in FIG. 1. Sidewall 105 of plasma chamber 100 has substrate port 107 that may be selectively sealed by a slit valve (not shown). Process gases are supplied to gas distribution assembly 121 by gas panel 130A coupled to port 130. One or more process gases may be supplied to toroidal sources 150A, 150B through gas panel 130B.

Referring to FIG. 1 again, plasma chamber 100 further contains controller 170 configured to monitor and control processes performed in plasma chamber 100. Controller 170 may be connected with one or more sensors and configured to sampling, analyzing and storing sensor data. In one embodiment, controller 170 may have the capacity to perform control tasks for different processes. Controller 170 may be connected to operating parts of plasma chamber 100 and send control signals to the operating parts. Controller 170 may perform a closed loop control task by adjusting process parameters according to sensor data to achieve desired process result. In one embodiment of the invention, controller 170 may be configured to perform dosage control of one or more species, end point detection, and other control tasks.

In one embodiment, optical sensor 730 is installed underneath substrate supporting surface 143, and is coupled to controller 170. Optical sensor 730 is adapted to detect light at a predetermined wavelength or frequency, which is emitted from the plasma generated in processing region 125. The emitted light may contain infrared light, visible light, ultraviolet light, or combinations thereof. In one embodiment, optical sensor 730 is configured to detect infrared light. When a substrate is processed in processing region 125, the emitted light is transmitted through the substrate placed on substrate supporting surface 143 before reaching optical sensor 730. When the dopant concentration in the substrate is low, light emitted from the plasma substantially transmits through the substrate to reach the underlying optical sensor 730. As the dopant concentration in the top surface of the substrate increases, the top surface of the substrate becomes opaque, causing less light to reach optical sensor 730. Based on the relationship between the dopant concentration in the substrate and the detected amount of light transmitted through the substrate, controller 170 is thus operable to determine a target dopant concentration of the substrate. Subsequently, the ion implantation process may be terminated.

Figure 3:
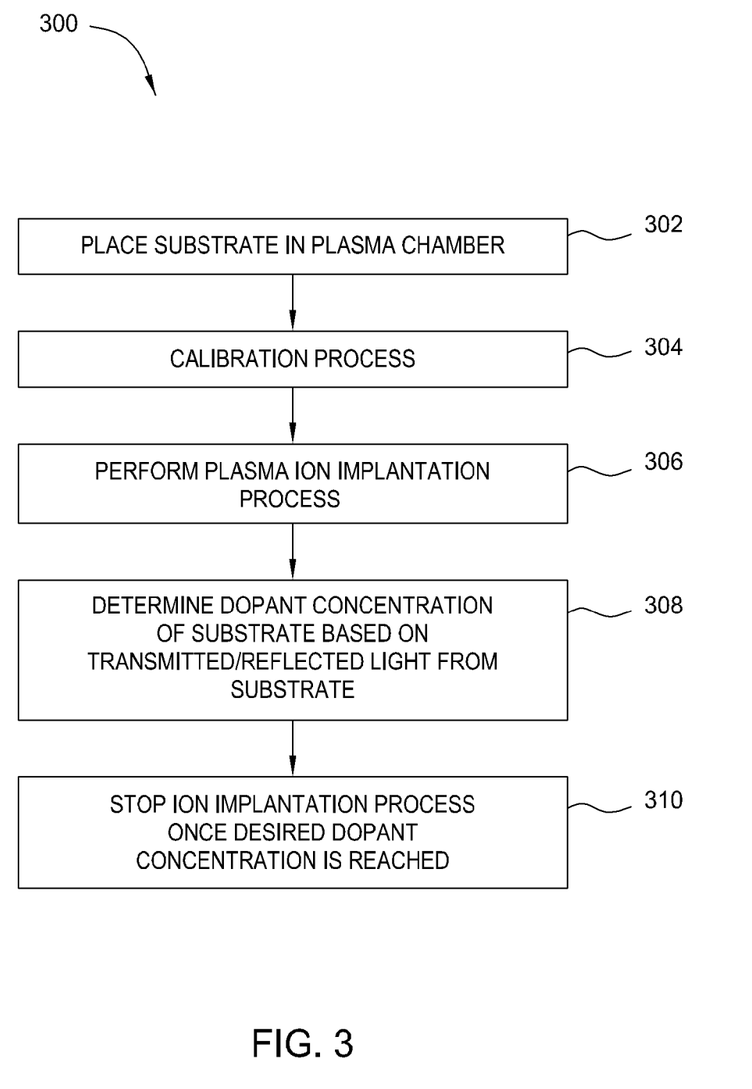
FIG. 3 illustrates a flowchart depicting a process for detecting an end point at a final dopant concentration during a plasma doping process, as described in embodiments herein.

FIG. 3 depicts a flowchart illustrating the steps of process 300 which may be used to detect an end point of a plasma ion implantation process, as described in embodiments herein. The illustrated method may be applicable to any of the embodiments shown in FIGS. 4-9B.

In step 302, substrate 702 to process is placed in the processing region 25 between perforated plate 132 and substrate supporting assembly 123. In step 304, optical sensor 730 and controller 170 are calibrated before starting the ion implantation process. In one embodiment, the calibration may be performed by generating radiation incident on substrate 702, detecting an amount of radiation received by optical sensor 730, and then associating a dopant concentration reference with the detected amount of radiation. In step 306, a plasma ion implantation then is performed to implant a dopant in substrate 702. In step 308, while the ion implantation is being conducted, controller 170 derives a current dopant concentration of the implanted dopant in substrate 702 based on an amount of radiation received by optical sensor 730. The radiation detected by optical sensor 730 may contain radiation transmitted through substrate 702 or reflected from substrate 702. In step 310, when the dopant concentration reaches the desired or final concentration, controller 170 outputs a control signal to stop the plasma ion implantation process.

Figure 4:
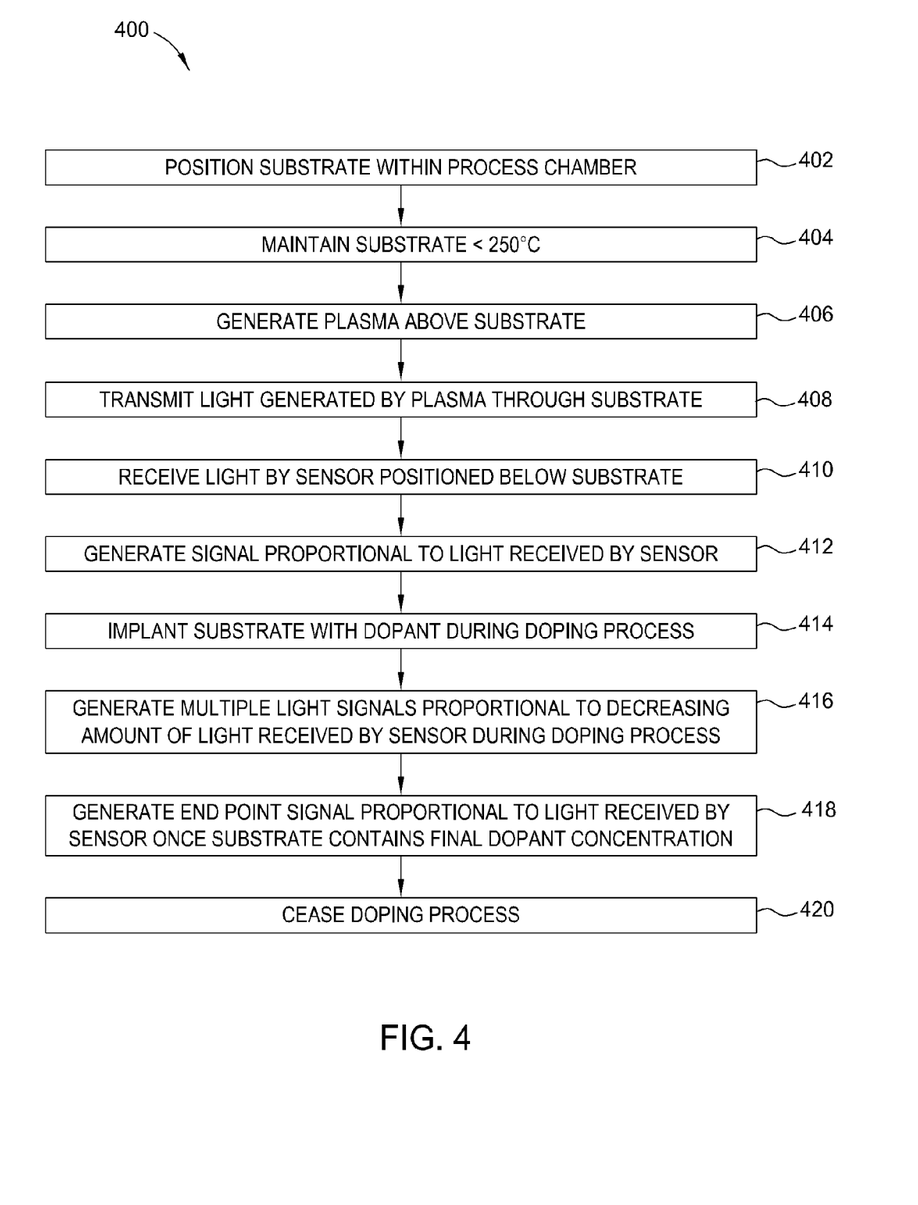
FIG. 4 illustrates a flowchart depicting another process for detecting an end point at a final dopant concentration during a plasma doping process, as described in an embodiment herein.

FIG. 4 illustrates a flowchart depicting process 400 that may be used to detect an end point at a final dopant concentration during a plasma doping process, as described in embodiments herein. In step 402, a substrate may be positioned within a process chamber, wherein the substrate has a topside and a backside. During the doping process at step 404, the substrate may be maintained, either by heating or cooling, at a temperature of less than about 250° C., preferably, within a range from about 0° C. to about 90° C., and more preferably, from about 25° C. to about 45° C. In step 406, a plasma is generated above the substrate within the process chamber. The light generated by the plasma is transmitted through the substrate during step 408. The light may contain infrared light, visible light, ultraviolet light, or combinations thereof. In one example, the light contains infrared light. The light enters the topside and exits the backside of the substrate. Thereafter, the light may be received by a sensor positioned below the substrate during step 410.

Process 400 further provides step 412 for generating a signal proportional to the light received by the sensor. Process 400 may be performed in a plasma chamber as configured in FIG. 5. Usually, the method includes generating multiple signals proportional to an increasing concentration of the dopant. During step 414, the substrate is implanted with a dopant during a doping process. Multiple light signals proportional to a decreasing amount of the light received by the sensor are generated at step 416 during the doping process. An end point signal proportional to the light received by the sensor once the substrate has a final concentration of the dopant is generated at step 418. Subsequently, the doping process is ceased at step 420 once the substrate contains the desired final, dopant concentration.

The substrate may be doped with a dopant, such as boron, phosphorous, arsenic, antimony, nitrogen, oxygen, hydrogen, carbon, germanium, or combinations thereof. The final dopant concentration of the substrate may be within a range from about $1 \times 10^{14}$ cm$^{-2}$ to about $1 \times 10^{18}$ cm$^{-2}$, preferably, from about $5 \times 10^{15}$ cm$^{-2}$ to about $1 \times 10^{17}$ cm$^{-2}$. In one example, the dopant is boron and the doping process includes exposing the substrate to a boron precursor, such as trifluoroborane, diborane, plasmas thereof, derivatives thereof, or combinations thereof. In another example, the dopant is phosphorous and the doping process includes exposing the substrate to a phosphorous precursor, such as trifluorophosphine, phosphine, plasmas thereof, derivatives thereof, or combinations thereof. In another example, the dopant is arsenic and the doping process includes exposing the substrate to an arsenic precursor, such as arsine, plasmas thereof, or derivatives thereof.

Figure 5:
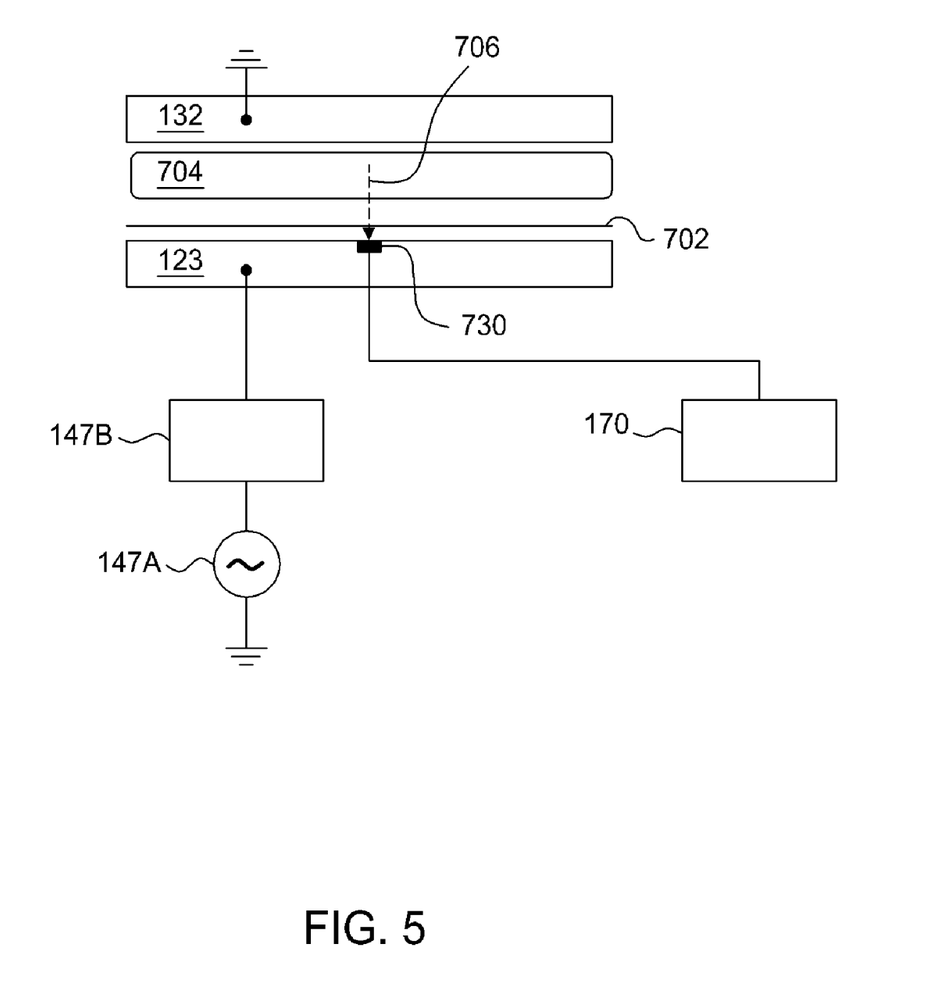
FIG. 5 is a simplified diagram illustrating how a dopant concentration in a substrate is controlled in real time with an optical sensor provided in the plasma chamber shown in FIG. 1.

FIG. 5 depicts an apparatus for determining an end point of a doping process while measuring dopant concentrations. The apparatus containing optical sensor 730 may be incorporated within plasma chamber 100 of FIG. 1, as well as used to perform process 400. Substrate 702 is exposed to a plasma 704 generated between perforated plate 132 and substrate support assembly 123. As illustrated, the perforated plate 121 may be grounded, and substrate supporting assembly 123 may be coupled to the RF plasma bias power 147A via RF impedance matching circuit 147B. Plasma 704 is generated by an RF power supplied by the RF plasma bias power 147A. Optical sensor 730 coupled to controller 170 is located below substrate 702.

Substrate 702 may be processed at a temperature of less than about 250° C., preferably, less than about 100° C., more specifically within a range from about 0° C. to about 90° C., preferably, from about 25° C. to about 45° C. As substrate 702 is processed in the plasma environment, radiation 706 emitted from plasma 704 transmit through substrate 702 and strike on optical sensor 730. In one embodiment, substrate 702 is transparent to radiation in a temperature environment less than about 250° C. In response to the detected radiation, optical sensor 730 issues a corresponding measure signal that is proportional to the detected amount of radiation to controller 170.

During operation, ion impurities may also be fed to dope substrate 702. Examples of used dopants that may contain, without limitation, boron, phosphorous, arsenic, antimony, nitrogen, oxygen, hydrogen, carbon, germanium, and combinations thereof. In the illustrated embodiment, boron dopants may be exemplary implanted in substrate 702 during a plasma implantation that uses diborane ($B_2H_6$) as the plasma precursor. The plasma thus may include boron ion species incident on the top surface of substrate 702. To control the dose of boron dopants implanted in substrate 702, controller 170 derives a dopant concentration of the implanted boron dopants based on the measure signal provided by optical sensor 730. While the ion implantation proceeds, the dopant concentration of boron dopants in substrate 702, which is derived by controller 170 in real time, increases as less radiation are transmitted through substrate 702. When the desired or final dopant concentration is reached, controller 170 outputs a control signal to stop the supply of the plasma precursor, which thereby terminates the ion implantation process. In one embodiment, the target dopant concentration is within a range from about $1\times10^{14}$ $cm^{-2}$ to about $1\times10^{18}$ $cm^{-2}$, and more preferably from about $5\times10^{15}$ $cm^{-2}$ to about $1\times10^{17}$ $cm^{-2}$.

As has been described above, a detected amount of radiation transmitted through the substrate is thus used to derive a dopant concentration in the substrate. However, in certain cases where the target dopant concentration in the substrate is relatively higher, the intensity of the radiation emitted from the plasma may not be sufficient to pass through the substrate as it becomes more opaque.

Figure 6:
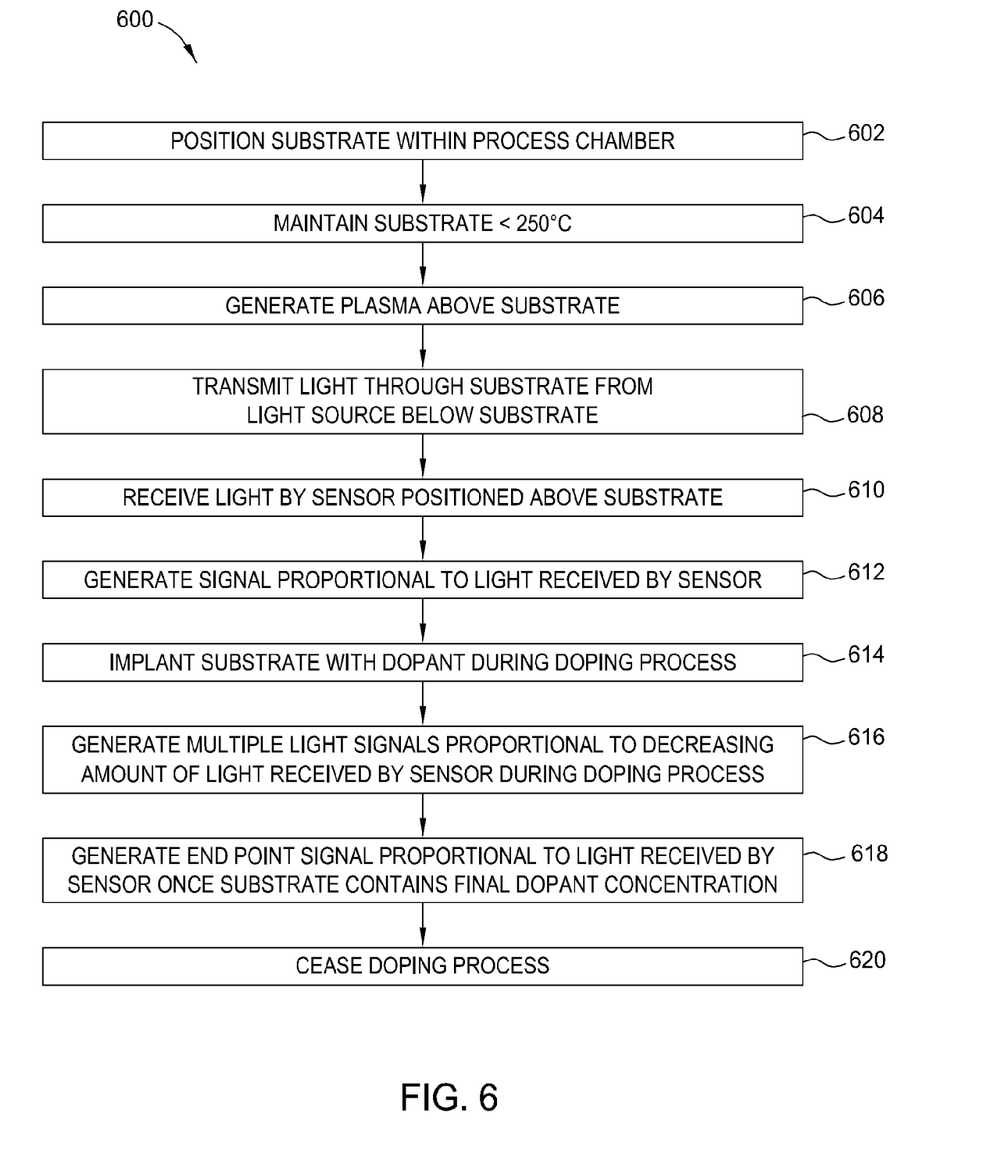
FIG. 6 illustrates a flowchart depicting another process for detecting an end point at a final dopant concentration during a plasma doping process, as described in another embodiment herein.

FIG. 6 illustrates a flowchart depicting process 600 that may be used to detect an end point at a final dopant concentration during a plasma doping process, as described in embodiments herein. Process 600 may be performed in a plasma chamber as configured in FIG. 7. In step 602, a substrate may be positioned within a process chamber, wherein the substrate has a topside and a backside. During step 604, the substrate may be maintained, either by heating or cooling, at a temperature of less than about 250° C., preferably, less than about 100° C., more specifically within a range from about 0° C. to about 90° C., preferably, from about 25° C. to about 45° C. In step 606, a plasma is generated above the substrate within the process or plasma chamber.

A light generated by a light source (e.g., laser source) is transmitted through the substrate during step 608. The light source is positioned below the substrate and a sensor is positioned above the substrate. Therefore, the light enters the backside and exits the topside of the substrate. The light is received by the sensor positioned above the substrate during step 610. The light may contain infrared light, visible light, ultraviolet light, or combinations thereof. In one example, the light contains infrared light, such as from an infrared laser.

In some examples, the sensor may be disposed on or coupled to a showerhead assembly (e.g., gas distribution assembly) within the process chamber. Also, the light source may be coupled to, within, or disposed on a substrate support assembly. In one example, the substrate support assembly may be an electrostatic chuck.

In a specific example, the sensor is disposed on or in a showerhead assembly and the light source is positioned to direct the light substantially towards the sensor. The light source may be an optical cable coupled to a remote light source, such as a laser source which emits a laser beam. In an alternative embodiment, a plasma light signal derived from light emitted from the plasma and is generated by the sensor. The magnitude of the plasma light signal may be subtracted from the magnitude of the light signal during a calibration step.

Process 600 further provides step 612 for generating a signal proportional to the light received by the sensor. Usually, the method includes generating multiple signals proportional to an increasing concentration of the dopant. During step 614, the substrate is implanted with a dopant during a doping process. Multiple light signals proportional to a decreasing amount of the light received by the sensor are generated at step 616 during the doping process. An end point signal proportional to the light received by the sensor once the substrate has a final dopant concentration of the substrate is generated at step 618. Subsequently, the doping process is ceased at step 620 once the substrate contains the desired dopant concentration.

The substrate may be doped with a dopant, such as boron, phosphorous, arsenic, antimony, nitrogen, oxygen, hydrogen, carbon, germanium, or combinations thereof. The final dopant concentration of the substrate may be within a range from about $1\times10^{14}$ $cm^{-2}$ to about $1\times10^{18}$ $cm^{-2}$, preferably, from about $5\times10^{15}$ $cm^{-2}$ to about $1\times10^{17}$ $cm^{-2}$. In one example, the dopant is boron and the doping process includes exposing the substrate to trifluoroborane, diborane, plasmas thereof, derivatives thereof, or combinations thereof. In another example, the dopant is phosphorous and the doping process includes exposing the substrate to trifluorophosphine, phosphine, plasmas thereof, derivatives thereof, or combinations thereof. In another example, the dopant is arsenic and the doping process includes exposing the substrate to arsine, plasmas thereof, or derivatives thereof.

Figure 7:
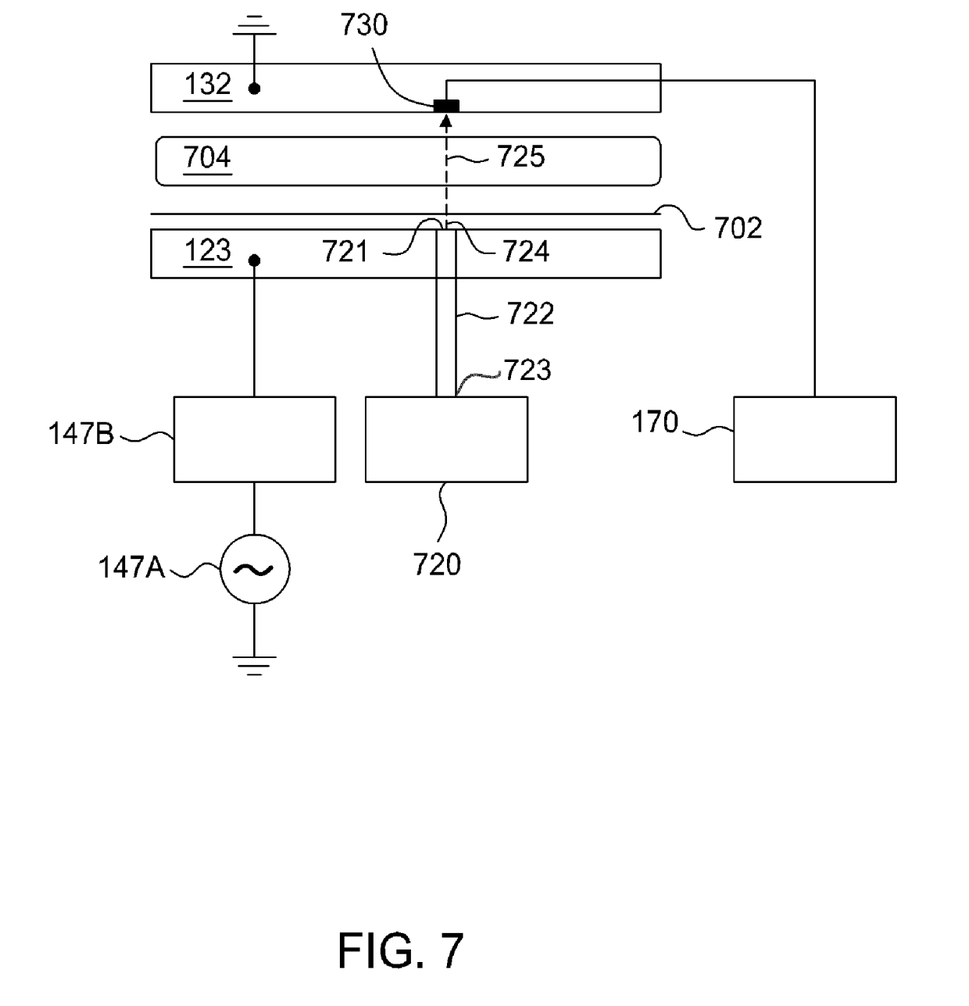
FIG. 7 illustrates an alternate embodiment that uses an optical sensor to detect an end point of a plasma ion implantation process.

FIG. 7 depicts an apparatus for determining an end point of a doping process while measuring dopant concentrations, which may be incorporated within plasma chamber 100 of FIG. 1, as well as used to perform process 600. The apparatus contains a light source 720, such as a laser source, that is connected to optical cable 722. Optical cable 722 may be guided through substrate support assembly 123. Optical sensor 730 is arranged above the top surface of substrate supporting assembly 123, facing the position of optical cable 722. In one embodiment, optical sensor 730 may be embedded in perforated plate 132.

In operation, optical cable 722 emits a light beam 724, such as a laser beam, from cable end 723 onto the backside of substrate 702. Light beam 724 may contain infrared light, visible light, ultraviolet light, or combinations thereof. The emitted light beam 724 transmits through substrate 702, and then strikes on optical sensor 730. During an ion implantation process, a transmitted portion 725 of the light beam 724 received by optical sensor 730 progressively decreases because substrate 702 becomes less transparent owing to an increase in the amount of dopants therein. Based on the amount of transmitted laser radiation received by optical sensor 730, controller 170 thus is able to derive the actual dopant concentration in substrate 702. When the target dopant concentration in substrate 702 is reached, controller 170 can output a control signal to terminate the ion implantation process.

Figure 8:
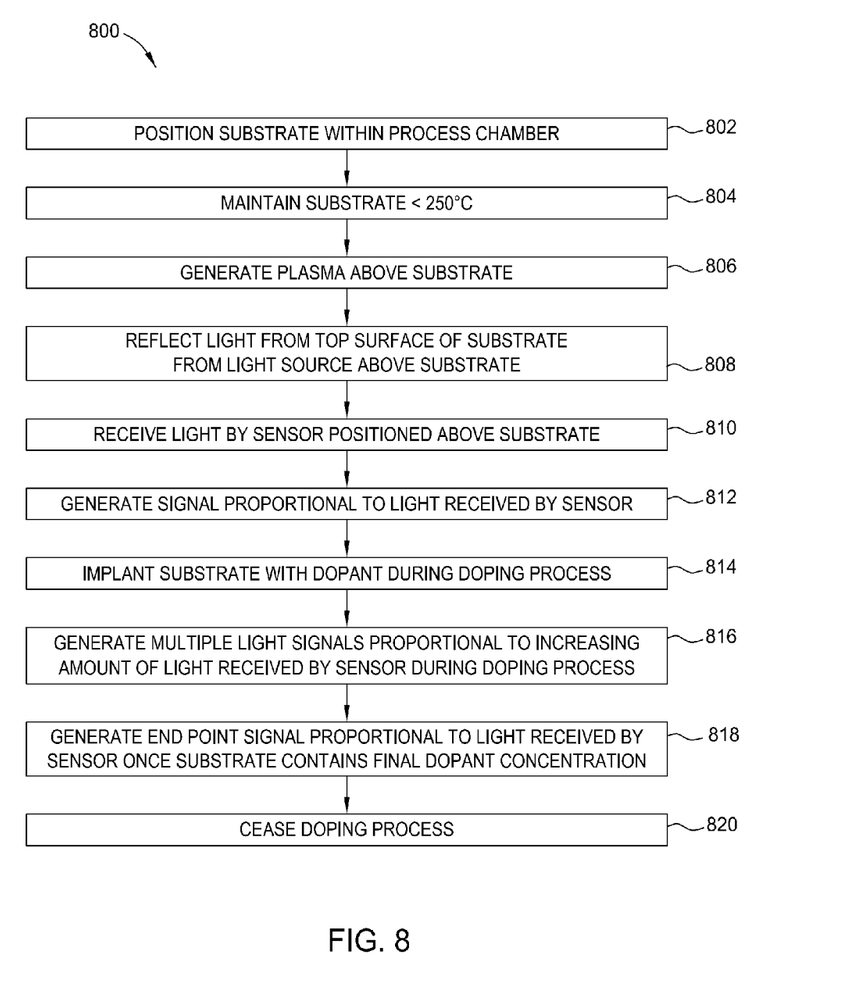
FIG. 8 illustrates a flowchart depicting another process for detecting an end point at a final dopant concentration during a plasma doping process, as described in another embodiment herein.

FIG. 8 illustrates a flowchart depicting process 800 that may be used to detect an end point at a final dopant concentration during a plasma doping process, as described in embodiments herein. Process 800 may be performed in a plasma chamber as configured in FIGS. 9A-9B. In step 802, a substrate may be positioned within a process chamber, wherein the substrate has a topside and a backside. During step 804, the substrate may be maintained, either by heating or cooling, at a temperature of less than about 250° C., preferably, less than about 100° C., more specifically within a range from about 0° C. to about 90° C., preferably, from about 25° C. to about 45° C. In step 806, a plasma is generated above the substrate within the process chamber.

A light generated by a light source (e.g., laser source) positioned above the substrate is transmitted to the topside of the substrate and reflected therefrom during step 808. The reflected light is received by a sensor positioned above the substrate during step 810. The light may contain infrared light, visible light, ultraviolet light, or combinations thereof. In one example, the light contains infrared light, such as from an infrared laser.

Embodiments provide that the light may be shined towards the topside of the substrate at an angle within a range from about 45° to about 90° relative to a plane expanding across the topside of the substrate. Preferably, the angle may be within a range from about 75° to about 90°, and more preferably, substantially about 90°. The light source may be coupled to or within the showerhead assembly, the sensor may be disposed on or coupled to the showerhead assembly, and the light source may be positioned to reflect the light off the substrate and towards the sensor.

The light source may be an optical cable coupled to a remote light source, such as a laser source which emits a laser beam. In one example, the substrate support assembly may be an electrostatic chuck. In other embodiments, the magnitude of the plasma light signal may be subtracted from the magnitude of the light signal during a calibration step.

Process 800 further provides step 812 for generating a signal proportional to the light received by the sensor. Usually, the method includes generating multiple signals proportional to an increasing concentration of the dopant. During step 814, the substrate is implanted with a dopant during a doping process. Multiple light signals proportional to an increasing amount of the light received by the sensor are generated at step 816 during the doping process. An end point signal proportional to the light received by the sensor once the substrate has a final dopant concentration of the substrate is generated at step 818. Subsequently, the doping process is ceased at step 820 once the substrate contains the desired dopant concentration.

The substrate may be doped with a dopant, such as boron, phosphorous, arsenic, antimony, nitrogen, oxygen, hydrogen, carbon, germanium, or combinations thereof. The final dopant concentration of the substrate may be within a range from about $1 \times 10^{14}$ cm$^{-2}$ to about $1 \times 10^{18}$ cm$^{-2}$, preferably, from about $5 \times 10^{15}$ cm$^{-2}$ to about $1 \times 10^{17}$ cm$^{-2}$. In one example, the dopant is boron and the doping process includes exposing the substrate to trifluoroborane, diborane, plasmas thereof, derivatives thereof, or combinations thereof. In another example, the dopant is phosphorous and the doping process includes exposing the substrate to trifluorophosphine, phosphine, plasmas thereof, derivatives thereof, or combinations thereof. In another example, the dopant is arsenic and the doping process includes exposing the substrate to arsine, plasmas thereof, or derivatives thereof.

Figure 9A:
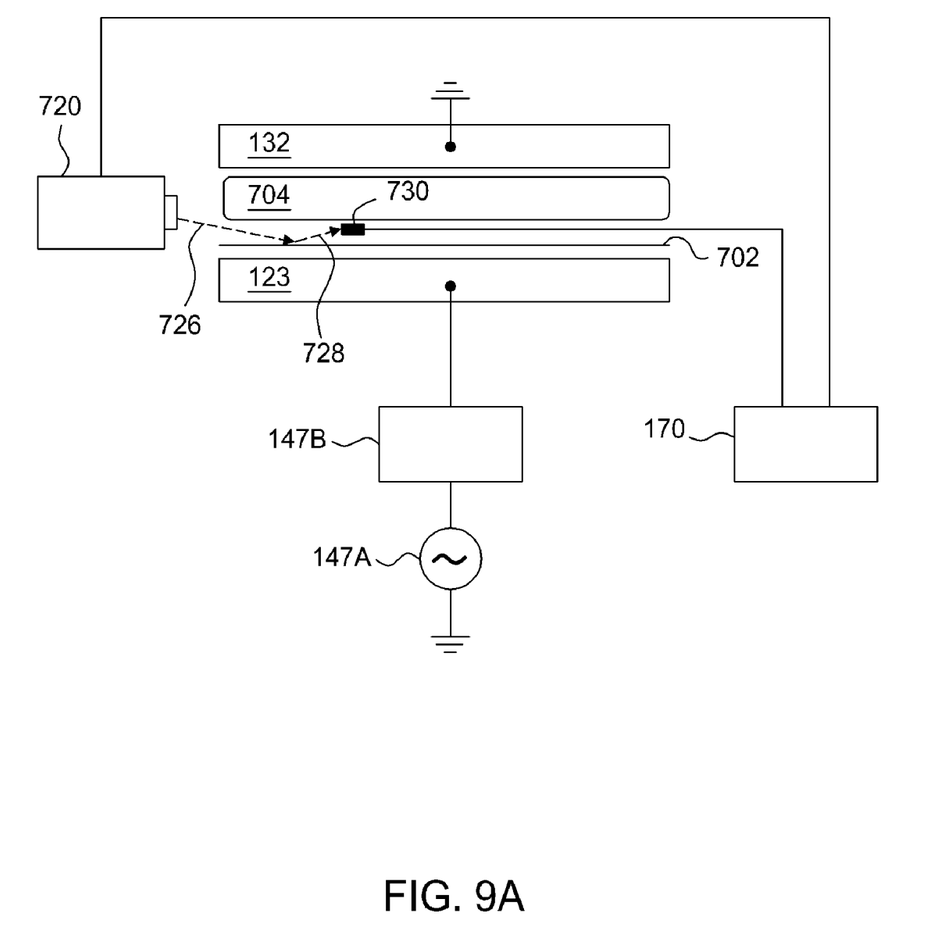
FIGS. 9A-9B illustrate other alternate embodiments that use an optical sensor to detect an end point of a plasma ion implantation process.
Figure 9B:
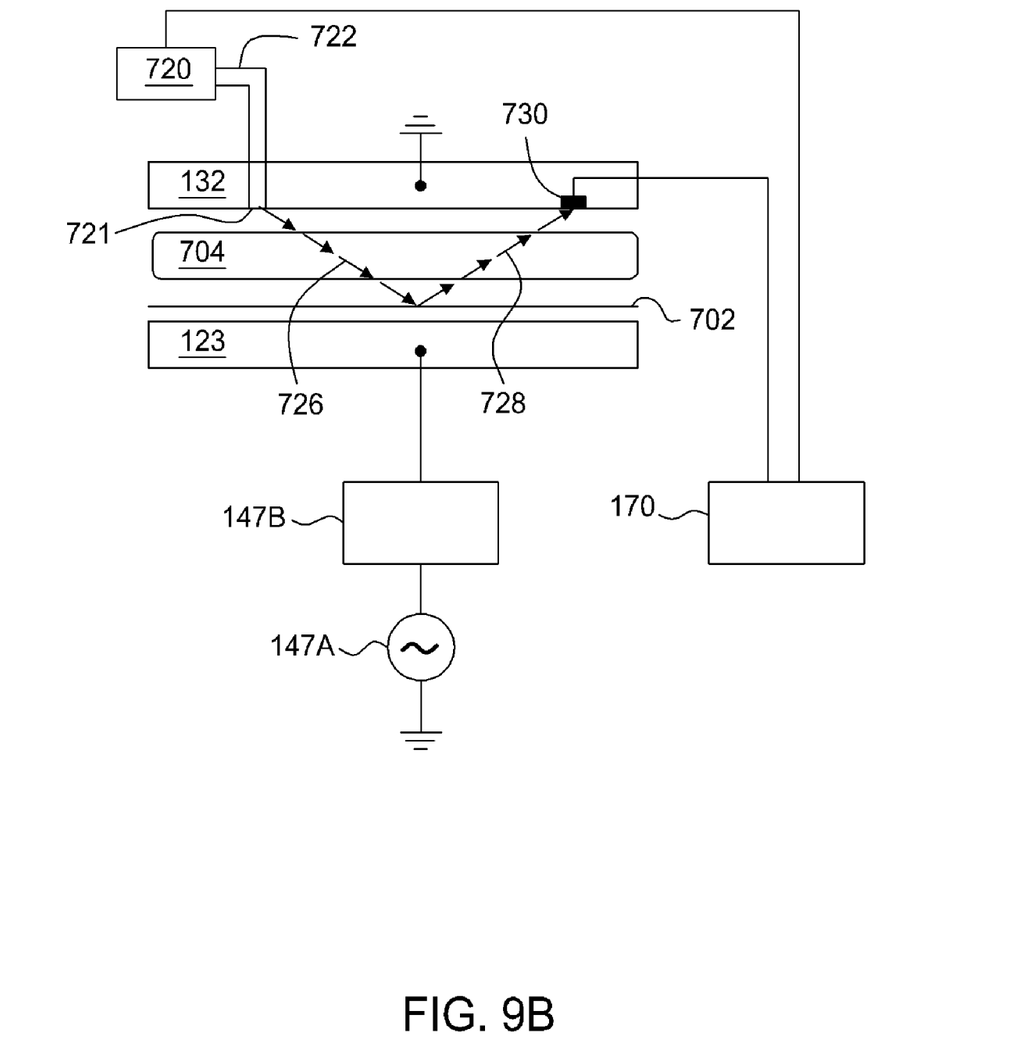

In another embodiment, FIG. 9A-9B depict an apparatus for determining an end point of a doping process while measuring dopant concentrations on the top surface of a substrate, which may be incorporated within plasma chamber 100 of FIG. 1, as well as used to perform process 800. As shown in FIGS. 9A-9B, light source 720 is placed approximately above the top surface of substrate supporting assembly 123, on the same side of the substrate as optical sensor 730. Substrate 702 is exposed to plasma 704 generated between perforated plate 132 and substrate support assembly 123.

In one embodiment, light source 720 is configured to emit an incident light beam 726, such as a laser beam, that is almost perpendicular to the normal of the top surface of substrate 702. Light beam 726 shines onto and reflects from the top surface of substrate 702 before it reaches optical sensor 730. When dopants are implanted in substrate 702, a reflected portion 728 of the incident light beam 726 received by optical sensor 730 is modulated by the progressively increasing dopant concentration within substrate 702. Based on the reflected portion 728 detected by optical sensor 730, controller 170 thus is able to derive the actual dopant concentration in substrate 702. When the desired, final dopant concentration in substrate 702 is reached, controller 170 outputs a control signal to terminate the ion implantation process. Light beam 726 may contain infrared light, visible light, ultraviolet light, or combinations thereof.

FIG. 9A illustrates light source 720 and optical sensor 730 both positioned above substrate 702. Light source 720 and optical sensor 730 may independently be coupled to or fixed on the chamber sidewalls, the chamber lid, the gas distribution assembly, such as perforated plate 132, or on another inner surface of the plasma chamber (not shown). FIG. 9B also depicts light source 720 and optical sensor 730 both positioned above substrate 702. In one embodiment, light source 720 may be a remote source of light, such as a laser source, that is connected to optical cable 722. Optical cable 722 may be guided through perforated plate 132. In operation, optical cable 722 emits light beam 726, such as a laser beam, from cable end 721 of optical cable 722.

It is understood that the methods and mechanisms described herein may be generally applicable to measure in real time the concentration of dopants being implanted into a substrate. This may be achieved by associating a specific level of infrared radiation with one particular type of dopant during calibration. Thus, the method and apparatus of the invention may be used to monitor and control dosage of a variety of dopants, such as arsenic, phosphorus, hydrogen, oxygen, fluorine, silicon, and other species used in a plasma process.

In another embodiment, a method for detecting a dopant concentration on a substrate surface during a plasma doping process is provided which includes positioning a substrate within a process chamber, wherein the substrate has a topside and a backside and is at a temperature of less than about 250° C., generating a plasma above the substrate within the process chamber, and transmitting a light through the substrate. The method further provides receiving the light by a sensor, generating an initial signal proportional to the light received by the sensor, implanting the substrate with a dopant during a dopant process, modulating the light received by the sensor proportional to an increasing dopant concentration, generating an end point signal proportional to the light received by the sensor once the substrate has a final dopant concentration of the substrate, and ceasing the implantation of the substrate by the dopant.

In one example, the light is generated by the plasma, the light received by the sensor is decreasing proportional to the increasing dopant concentration, and the sensor is positioned below the substrate. In another example, the light is generated by a light source (e.g., laser source) positioned below the substrate, the light received by the sensor is decreasing proportional to the increasing dopant concentration, and the sensor is positioned below the substrate. In another example, the light is generated by a light source positioned above the substrate, the light received by the sensor is increasing proportional to the increasing dopant concentration, and the sensor is positioned above the substrate.

In another embodiment, a method for detecting a dopant concentration on a substrate surface during a plasma doping process is provided which includes positioning a substrate within a process chamber, wherein the substrate has a topside and a backside and is at a temperature of less than about 250° C., generating a plasma above the substrate within the process chamber, reflecting a light from the topside of the substrate, and receiving the light by a sensor. The method further provides generating an initial signal proportional to the light received by the sensor, implanting the substrate with a dopant during a dopant process, increasing the light received by the sensor proportional to an increasing dopant concentration generating an end point signal proportional to the light received by the sensor once the substrate has a final dopant concentration of the substrate, and ceasing the implantation of the substrate by the dopant.

In another embodiment, the multiple optical sensors disposed below the substrate, such as within a substrate support assembly, optical sensors may be adapted to monitor the uniformity of the dopant concentration across the substrate surface.

While the foregoing is directed to embodiments of the invention, other and further embodiments of the invention may be devised without departing from the basic scope thereof, and the scope thereof is determined by the claims that follow.

The invention claimed is:

1. A method for detecting a doping concentration on a substrate surface during a plasma doping process, comprising:
   maintaining a substrate at a temperature of less than about 250° C. within a process chamber, wherein the substrate has a topside and a backside;
   generating a plasma above the topside of the substrate within the process chamber;
   transmitting a light through the substrate;
   receiving the light by a sensor;
   generating an initial signal proportional to the light received by the sensor;
   implanting the substrate with a dopant during a dopant process;
   modulating the light received by the sensor proportional to an increasing dopant concentration;
   generating an end point signal proportional to the light received by the sensor once the substrate comprises a final concentration of the dopant; and
   ceasing the dopant implantation of the substrate.

2. The method of claim 1, wherein the light is generated by the plasma, the light received by the sensor is decreasing proportional to the increasing dopant concentration, and the sensor is positioned below the backside of the substrate.

3. The method of claim 1, wherein the light is generated by a laser positioned below the backside of the substrate, the light received by the sensor is decreasing proportional to the increasing dopant concentration, and the sensor is positioned above the topside of the substrate.

4. The method of claim 1, wherein the light is generated by a laser positioned above the topside of the substrate, the light received by the sensor is increasing proportional to the increasing dopant concentration, and the sensor is positioned above the topside of the substrate.

5. The method of claim 1, wherein the light comprises infrared light, visible light, ultraviolet light, or combinations thereof.

6. The method of claim 5, wherein the light comprises infrared light.

7. The method of claim 5, wherein the temperature of the substrate is within a range from about 0° C. to about 90° C. during the doping process.

8. The method of claim 1, wherein the dopant is selected from the group consisting of boron, phosphorous, arsenic, antimony, nitrogen, oxygen, hydrogen, carbon, germanium, and combinations thereof.

9. The method of claim 8, wherein the final concentration of the dopant is within a range from about $5 \times 10^{15}$ cm$^{-2}$ to about $1 \times 10^{17}$ cm$^{-2}$.

10. The method of claim 8, wherein the dopant is boron and the doping process comprises exposing the substrate to trifluoroborane, diborane, plasmas thereof, derivatives thereof, or combinations thereof.

11. The method of claim 8, wherein the dopant is phosphorous and the doping process comprises exposing the substrate to trifluorophosphine, phosphine, plasmas thereof, derivatives thereof, or combinations thereof.

12. The method of claim 8, wherein the dopant is arsenic and the doping process comprises exposing the substrate to arsine, plasmas thereof, or derivatives thereof.

13. A method for detecting a doping concentration on a substrate surface during a plasma doping process, comprising:
   maintaining a substrate a temperature of less than about 250° C. within a process chamber, wherein the substrate has a topside and a backside;
   generating a plasma above the topside of the substrate within the process chamber;
   reflecting a light from the topside of the substrate;
   receiving the light by a sensor;
   generating an initial signal proportional to the light received by the sensor;
   implanting the substrate with a dopant during a dopant process;
   increasing the light received by the sensor proportional to an increasing dopant concentration;
   generating an end point signal proportional to the light received by the sensor once the substrate comprises a final concentration of the dopant; and
   ceasing the dopant implantation of the substrate.

14. The method of claim 13, wherein the light comprises infrared light, visible light, ultraviolet light, or combinations thereof.

15. The method of claim 14, wherein the light comprises infrared light.

16. The method of claim 14, wherein the temperature of the substrate is within a range from about 0° C. to about 90° C. during the doping process.

17. The method of claim 13, wherein the dopant is selected from the group consisting of boron, phosphorous, arsenic, antimony, nitrogen, oxygen, hydrogen, carbon, germanium, and combinations thereof.

18. The method of claim 17, wherein the final concentration of the dopant is within a range from about $5 \times 10^{15}$ cm$^{-2}$ to about $1 \times 10^{17}$ cm$^{-2}$.

19. The method of claim 17, wherein the dopant is boron and the doping process comprises exposing the substrate to trifluoroborane, diborane, plasmas thereof, derivatives thereof, or combinations thereof.

20. The method of claim 17, wherein the dopant is phosphorous and the doping process comprises exposing the substrate to trifluorophosphine, phosphine, plasmas thereof, derivatives thereof, or combinations thereof, or the dopant is arsenic and the doping process comprises exposing the substrate to arsine, plasmas thereof, or derivatives thereof.

* * * * *